United States Patent [19]

DeLuca et al.

[11] 4,338,250
[45] Jul. 6, 1982

[54] 1-HYDROXYLATION PROCESS

[75] Inventors: Hector F. DeLuca; Heinrich K. Schnoes, both of Madison, Wis.; David E. Hamer, Hyattsville, Md.; Herbert E. Paaren, Madison, Wis.

[73] Assignee: Wisconsin Alumni Research Foundation, Madison, Wis.

[21] Appl. No.: 258,125

[22] Filed: Apr. 27, 1981

[51] Int. Cl.³ .................................................. C07J 9/00
[52] U.S. Cl. .................................................. 260/397.2
[58] Field of Search ...................... 260/397.2; 424/236

[56] References Cited

U.S. PATENT DOCUMENTS

| | | | |
|---|---|---|---|
| 3,847,955 | 11/1974 | DeLuca et al. | 260/397.2 |
| 4,022,891 | 5/1977 | Takeshita et al. | 260/397.2 |
| 4,202,829 | 5/1980 | DeLuca et al. | 260/397.2 |
| 4,206,131 | 6/1980 | Salmond | 260/397.2 |

Primary Examiner—Elbert L. Roberts
Attorney, Agent, or Firm—Howard W. Bremer

[57] ABSTRACT

A process for preparing biologically active 1α-hydroxyvitamin D compounds from vitamin D compounds by hydroxylation at carbon 1 and subsequent photochemical isomerization, and novel intermediates and products resulting from this process are provided.

21 Claims, No Drawings

1-HYDROXYLATION PROCESS

The invention described herein was made in the course of work under a grant or award from the Department of Health and Human Services.

DESCRIPTION

This invention relates to the preparation of biologically active vitamin D derivatives.

More specifically, this invention relates to a convenient novel process for the preparation of 1α-hydroxyvitamin D compounds, and of intermediates used in such a process.

It is well known that biological activity of the D vitamins (e.g. vitamin $D_3$ or vitamin $D_2$) depends on their metabolism in vivo to hydroxylated forms. For example, vitamin $D_3$ undergoes two successive hydroxylations leading first to 25-hydroxyvitamin $D_3$ (25-OH-$D_3$) and then to 1α,25-dihydroxyvitamin $D_3$ (1α,25-$(OH)_2D_3$). It is the latter compound that exhibits the most potent biological activity in vivo, and is thought to be the most important vitamin D-derived agent for the regulation of calcium metabolism and the calcification of bone in the animal or human. In addition, it has been established that certain 1α-hydroxylated analogs of the natural metabolites, e.g. 1α-hydroxyvitamin $D_3$ or 1α-hydroxyvitamin $D_2$, exhibit very high biological activity in vivo, and it is now clear that the 1α-hydroxylated vitamin D metabolites as well as some of their 1α-hydroxylated analogs will have important utility in the treatment or prevention of a variety of calcium metabolism disorders in the animal or human, especially bone diseases of the human. In consequence of this apparent utility, the preparation of 1α-hydroxyvitamin D compounds has received much attention, as amply documented in the patent or other literature, for example, in U.S. Pat. No. 3,741,996 directed to 1α-hydroxycholecalciferol, U.S. Pat. No. 3,906,014 directed to 3-deoxy-1α-hydroxycholecalciferol, U.S. Pat. No. 3,907,843 directed to 1α-hydroxyergocalciferol, U.S. Pat. Nos. 3,901,928 and 3,966,777 directed to processes for the production of 1α-hydroxyvitamin $D_3$, U.S. Pat. Nos. 4,195,027, 4,202,829, 4,206,131 and 4,234,495 directed to the preparation of a variety of 1α-hydroxyvitamin D compounds.

Most available chemical processes for the preparation of 1α-hydroxyvitamin D compounds involve the hydroxylation of a suitable steroid and its subsequent conversion to the desired vitamin (see for example the review by DeLuca et al., in Topics in Current Chemistry, Vol. 83, pp. 1–65, Springer-Verlag, Berlin, Heidelberg, 1979), although more direct and efficient hydroxylation sequences via cyclovitamin D intermediates (DeLuca et al., U.S. Pat. Nos. 4,195,027 and 4,234,495) or via organo-selenium intermediates (Salmond, U.S. Pat. No. 4,206,131) have recently been proposed.

Conceptually the most expeditious approach to 1α-hydroxyvitamin D derivatives is the direct allylic oxidation at carbon 1 of the readily available vitamin D compounds, e.g. vitamin $D_3$, vitamin $D_2$, 25-hydroxyvitamin $D_3$, 25-hydroxyvitamin $D_2$, 24,25-dihydroxyvitamin $D_3$, 25,26-dihydroxyvitamin $D_3$ and related analogs. Such a direct C-1 hydroxylation of vitamin D compounds has been accomplished by Pelc (Steroids, 30, 193, 1977) and DeLuca et al. (Proc. Natl. Acad. Sci. USA, 75, 2080, 1978, and U.S. Pat. No. 4,202,829) who show, for example, the preparation of 1α-hydroxyvitamin $D_3$ and 1,25-dihydroxyvitamin $D_3$ from vitamin $D_3$ and 25-hydroxyvitamin $D_3$ by allylic oxidation using selenium dioxide. However, the yields of the 1α-hydroxy compounds are very poor (e.g. 0.5–1%) and the desired compounds were accompanied by several undesired isomeric products (e.g. 1β-hydroxyvitamin $D_3$, and double-bond isomers) as well as decomposition products. Such process is, therefore, seriously lacking in efficiency and specificity and these deficiencies limit its practical application.

A new process devoid of these deficiencies has now been developed which allows for the two-step conversion of vitamin D compounds (5,6-cis double bond geometry) to the corresponding 1α-hydroxyvitamin D compounds. This process is depicted in the scheme below and comprises the treatment of 5,6-cis-vitamin $D_3$ starting material of general structure I with a novel and surprisingly efficacious combination of reagents to yield 1α-hydroxy-5,6-trans-vitamin D compounds of general structure II which are converted to the desired 1α-hydroxyvitamin D compounds (III) by known irradiation methods preferably in the presence of a photosensitizer. In the overall process, the desired 1α-hydroxyvitamin D products are obtained in a yield comparing favorably with available alternative processes. In addition, the present 1-hydroxylation method is highly advantageous because of its brevity and the ease with which it can be carried out, as is evident from the scheme below.

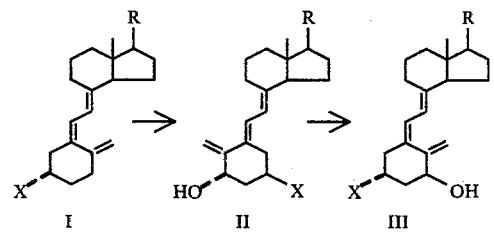

In the above structures, X represents hydrogen, hydroxy or a protected-hydroxy group, and R represents any sidechain substituent that is desired in the final product. R may be, for example, hydrogen or alkyl (e.g. methyl, ethyl, propyl, isopropyl, isobutyl), or a hydroxy- or keto-containing-alkyl residue (e.g. acetyl, hydroxymethyl, hydroxyethyl, etc.), or a sidechain as it occurs in vitamin D compounds and related analogs which may be represented by the structures below

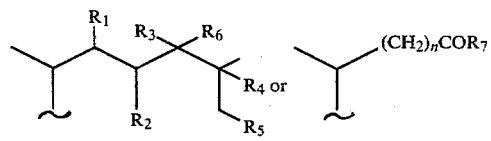

wherein each of $R_1$ and $R_2$ is selected from the group consisting of hydrogen, hydroxy, protected hydroxy and fluoro, or where $R_1$ and $R_2$ when taken together form a double bond or an epoxide grouping, where each of $R_3$, $R_4$ and $R_5$ is selected from the group consisting of hydrogen, hydroxy, protected-hydroxy and fluoro, or where $R_3$ and $R_4$, or $R_4$ and $R_5$, when taken together, form an epoxide grouping or a double bond, where $R_6$ is hydrogen, alkyl or fluoro, where $R_7$ is hydroxy, alkyl or O-alkyl, and n is an integer from 1 to 4 inclusive.

As used in this specification, a "protected hydroxy" is a hydroxy function protected by acylation, alkylation or silylation, etc., i.e. existing as an O-acyl, O-alkyl or O-alkylsilyl derivative. The word "acyl" means an aliphatic acyl group having from 1 to about 5 carbon atoms, e.g. acetyl, propionyl, butyryl, pentoyl, etc. and the isomeric forms thereof, or an aromatic acyl group such as benzoyl, halobenzoyl, or nitrobenzoyl. The word "alkyl" connotes an aliphatic alkyl group of from 1 to about 5 carbon atoms, in all its isomeric forms, e.g. methyl, ethyl, propyl, isopropyl, butyl, isobutyl, etc. Vitamin D starting materials, characterized by the presence of sidechain substituents as defined by R above are available as natural or synthetic products (see for example, DeLuca et al., in Topics in Current Chemistry, Vol. 83, pp. 1–65, Springer Verlag, Berlin/Heidelberg, 1978; Schnoes and DeLuca, Fed. Proc. 39, 2723–2729, 1980; Jones et al., Arch. Biochem. Biophys. 202, 450–457, 1980).

The first step of the process of this invention comprises the treatment of the vitamin D starting material of general structure I above, dissolved in a suitable solvent (e.g. an ether solvent, or a halocarbon solvent such as methylene chloride, carbon tetrachloride, dichloroethane, dichloropropane, etc.) with iodine, and a solution of a combined oxidant consisting of $SeO_2$ and a hydroperoxide. Suitable hydroperoxides are hydrogen peroxide or alkyl hydroperoxides, e.g. t-butyl hydroperoxide with the latter being the preferred reactant. The reaction is normally conducted with catalytic amount of $SeO_2$-oxidant (e.g. ca. 0.25 equivalents relative to the vitamin D compound to be oxidized) but stoichiometric amounts can also be used effectively. The hydroperoxide is present in excess over the $SeO_2$ oxidant (e.g. 10–30 equivalents excess). Also, the presence of a nitrogenous base in the reaction mixture is highly beneficial to achieve the preferred formation of 1α-hydroxylated product. Pyridine is a convenient nitrogenous base for this purpose, since it can serve simultaneously as the solvent for the iodine and the oxidant mixture, and as cosolvent for the reaction; the pyridine advantageously comprising about 30–50% (by volume) of the reaction solvent mixture. Nitrogenous bases other than pyridine can, however, also be used effectively in this process. Exemplary of such other nitrogen bases are substituted pyridines (e.g. the picolines), collidine, quinoline, octahydroacridine, or pyrazoles. Nitrogen compounds that are solids are, of course, added as solutions (e.g. halocarbon solutions) in sufficient amounts to achieve an excess of nitrogen base over the vitamin D compound (e.g. 3–10 molar excess) used as the starting material. The reaction can be conducted over a wide range of temperatures, with a range from about 0° C. to about room temperature being preferred. Reaction time varies with temperature and amount of $SeO_2$-oxidant, and it is advantageous therefore to monitor the progress of the reaction (i.e. formation of 1-hydroxy-5,6-trans-vitamin D product) by standard analytical methods, e.g. thin layer chromatography. With catalytic amounts of oxidant at room temperature ca. 1–2 hr reaction time is appropriate; at lower temperatures longer times are required, but increased oxidant will shorten the reaction time.

The product of this reaction is the 1-hydroxy-5,6-trans-vitamin D compound, corresponding to the vitamin D compound used as the starting material. This product is isolated in ca. 30–40% yield as an approximately 2:1 mixture of 1α-hydroxy-5,6-trans-vitamin D compound and the corresponding 1β-hydroxy-epimer. Essentially no 1-hydroxy-5,6-cis-vitamin D products are formed under these conditions.

The desired 1α-hydroxy-5,6-transvitamin D compound of general structure II above, can be isolated by careful chromatography, but preferably, and particularly when larger quantities are involved, and when the substituent X in structure II is hydroxy, it is separated and purified from the epimer product mixture by a novel procedure which comprises treatment of a solution of the epimer mixture (e.g. ether, tetrahydrofuran or hydrocarbon solutions) with an alkyl- or arylboronic acid (e.g. phenylboronic acid) at about room temperature so as to form a cyclic 1,3-boronate ester with the undesired 1β-hydroxy-5,6-trans-vitamin D product (having 1,3-cis-diol configuration). The mixture of nonpolar vitamin D-boronate ester and polar, free 1α-hydroxy-5,6-trans-vitamin D product is then easily separated by simple column chromatography (or related separation methods) to obtain the desired 1α-hydroxy-5,6-trans-vitamin D compound of general structure II above in pure form, and in ca. 15–20% overall yield based on vitamin D starting material used.

It should be obvious that this separation of 1α-hydroxy and 1β-hydroxy epimers by boronate ester formation with the undesired epimer having the 1,3-cis diol configuration can be carried out effectively also after the photochemical isomerization of the 5,6-trans-vitamin D compounds to the corresponding 5,6-cis-vitamin D products which is described below. The method is, in fact, generally applicable to the separation of vitamin D-1,3-diols (or 5,6-trans-vitamin D-1,3-diols) having the 1,3-trans diol configuration from the corresponding epimers having the 1,3-cis-diol configuration.

The 1α-hydroxylated 5,6-trans product (formula II, above) is isomerized in a final step to the corresponding 1α-hydroxyvitamin D compound (5,6-cis double bond geometry) of general structure III as shown above. This isomerization is accomplished by known photochemical methods, e.g. actinic irradiation of a solution of the 5,6-trans compound according to the method of Inhoffen et al. (Chem. Ber. 90, 2544, 1957) which yields a mixture of 5,6-trans starting material and the desired 5,6-cis product. Preferably, however, the isomerization is conducted according to the procedure of Gielen et al. (Recueil, J. Roy. Netherlands Chem. Society, 99, 306–311, 1980), which comprises actinic irradiation of a solution of 5,6-trans compound in the presence of a photosensitizer. Any light source emitting radiation suitable for the excitation of the photosensitizer is effective, but it is preferable that light of a wavelength of less than about 310 nm be excluded, by suitable choice of light source or filters. Suitable photosensitizers are compounds such as anthracene, acridine or phenazine. It has been found desirable to have these photosensitizers present in large excess (e.g. 5–10 fold molar excess). Toluene or benzene are suitable solvents for use in the isomerization procedure; it being desirable to maintain the solution under an inert atmosphere (nitrogen, argon) at low temperature (e.g. 0°–10° C.). Under these conditions, toluene is a preferred solvent since benzene freezes at about 5° C. This general procedure provides for the nearly quantitative conversion of the 1α-hydroxy-5,6-trans-vitamin D compound to the desired 1α-hydroxyvitamin D product (structure III, above).

The oxidation (1α-hydroxylation) step described above, in combination with the photosensitized isomerization procedure yields the desired 1α-hydroxyvitamin D compound of general structure III above from the corresponding vitamin D starting material of general formula I above in a most efficient and convenient manner. The following conversions, which can be readily accomplished, are illustrative of the scope and versatility of the method.

vitamin $D_3 \rightarrow 1\alpha$-hydroxy-5,6-trans-vitamin $D_3 \rightarrow 1\alpha$-hydroxyvitamin $D_3$ vitamin $D_2 \rightarrow 1\alpha$-hydroxy-5,6-trans-vitamin $D_2 \rightarrow 1\alpha$-hydroxyvitamin $D_2$ 25-hydroxyvitamin $D_3 \rightarrow 1\alpha,25$-dihydroxy-5,6-trans-vitamin $D_3 \rightarrow 1\alpha,25$-dihydroxyvitamin $D_3$ 24,25-dihydroxyvitamin $D_3 \rightarrow 1\alpha,24,25$-trihydroxy-5,6-trans-vitamin $D_3 \rightarrow 1\alpha,24,25$-trihydroxyvitamin $D_3$ 25,26-dihydroxyvitamin $D_3 \rightarrow 1\alpha,25,26$-trihydroxy-5,6-trans-vitamin $D_3 \rightarrow 1\alpha,25,26$-trihydroxyvitamin $D_3$ 25-hydroxyvitamin $D_2 \rightarrow 1\alpha,25$-dihydroxy-5,6-trans-vitamin $D_2 \rightarrow 1\alpha,25$-dihydroxyvitamin $D_2$ 24,25-dihydroxyvitamin $D_2 \rightarrow 1\alpha,24,25$-trihydroxy-5,6-trans-vitamin $D_2 \rightarrow 1\alpha,24,25$-trihydroxyvitamin $D_2$ 25-keto-27-norvitamin $D_3 \rightarrow 1\alpha$-hydroxy-25-keto-27-nor-5,6-trans-vitamin $D_3 \rightarrow 1\alpha$-hydroxy-25-keto-27-norvitamin $D_3$ 26,27-bisnorvitamin $D_3$-25-carboxylic acid methyl ester $\rightarrow 1\alpha$-hydroxy-26,27-bisnor-5,6-trans-vitamin $D_3$-25-carboxylic acid methyl ester $\rightarrow 1\alpha$-hydroxy-26,27-bisnorvitamin $D_3$-25-carboxylic acid methyl ester Vitamin D compounds with protected hydroxy groups (e.g. O-acyl or O-alkylsilyl groups) are of course equally suitable as starting material for this $1\alpha$-hydroxylation process, such protecting groups being capable of ready removal, if the free vitamin sterol is desired, either after formation of the $1\alpha$-hydroxy-5,6-trans-vitamin D product or after the subsequent photochemical conversion step, by procedures well known in the art, e.g. mild base hydrolysis (5% KOH/MeOH), or hydride reduction, for the removal of acyl groups, and hydrolysis in protic solvents for the removal of alkylsilyl groups.

The present invention is more specifically described by the following illustrative examples.

EXAMPLE 1

Synthesis of 5,6-trans-1α-hydroxyvitamin $D_3$ from vitamin $D_3$

To a 100 ml, 3-necked, round-bottomed flask equipped with a rubber septum and nitrogen filled balloon is added 501.7 mg (1.31 mmol) of vitamin $D_3$ followed by 35 ml of dichloroethane. A charge of 1 mg of iodine in 50 μl of pyridine is added and the resulting yellowish solution stirred at room temperature under nitrogen atmosphere for 90 min. Separately, a solution of 50 mg (0.45 mmol) of selenium dioxide in 25 ml of pyridine and 1 ml of t-butylhydroperoxide is prepared. Both solutions are cooled at 4° C. for 1 h then the selenium dioxide solution is added to the vitamin solution through the rubber septum. Stirring under nitrogen atmosphere is continued at 4° C. for 12.5 h then the reaction is worked up by pouring the reaction mixture onto a cooled, brine-saturated mixture of 250 ml of ether, 50 ml of 1 N sodium hydroxide solution and 25 ml of 1% sodium thiosulfate solution. After phase separation the ether layer is washed with water (25 ml, 3×), 10% aqueous acetic acid (30 ml, 2×), water (25 ml, 3×), 1 N sodium hydroxide solution (25 ml, 3×) and water (25 ml, 3×). After evaporation of the solvent 689.3 mg of crude product is recovered. The crude product is dissolved in 50 ml of ether and 60 mg of phenylboronic acid is added. After 15 min of reaction, thin layer chromatography (5% methanol in chloroform, silica gel) indicates the spot co-migrating with a known sample of 5,6-trans-1β-hydroxyvitamin $D_3$ has disappeared. The solvent is evaporated and the residue applied in 20% ethyl acetate in hexane to a 2×36 cm silica gel column followed by elution with ethyl acetate/hexane mixtures. The column fractions are assayed by TLC and those fractions containing material of similar polarity to 1-hydroxylated vitamin $D_3$ compounds are pooled to give, after evaporation of solvent, 86 mg (16% yield) of a whitish powder shown to be identical with 5,6-trans-1α-hydroxyvitamin $D_3$ by comparison of the sample's NMR, UV and mass spectra with those of an authentic sample of this compound: UV (EtOH) $\lambda_{max}$ 272 nm (ε 23,800); $^1$H-NMR (270 MHz) δ0.56 (3H, s, 18-Me), 0.86 (6H, d, J6.6 Hz, 26,27-Me), 0.92 (3H, d, J6.0 Hz, 21-Me), 4.23 (1H, m, 3-H), 4.49 (1H, m, 1-H), 4.97 (1H, m (sharp), (19Z)-H), 5.12 (1H, m (sharp), (19E)-H) and 5.90 and 6.58 (2H, ABq, J=11.2 Hz, 6- and 7-H), mass spectrum (70 eV), m/e (relative intensity) 400 (M+, 13%), 382 (8), 364(4), 152(35), and 134(100). Application of the above procedure to other vitamin D compounds or vitamin D metabolites, such as 25-hydroxyvitamin $D_3$, 24,25-dihydroxyvitamin $D_3$, or 25,26-dihydroxyvitamin $D_3$ yields, respectively, 1α,25-dihydroxy-5,6-trans-vitamin $D_3$, 1α,24,25-trihydroxy-5,6-trans-vitamin $D_3$ and 1α,25,26-trihydroxyvitamin $D_3$.

EXAMPLE 2

Synthesis of 5,6-trans-1α-hydroxyvitamin $D_2$ from vitamin $D_2$

A sample of vitamin $D_2$ (515.2 mg, 1.30 mmol) is treated with iodine followed by selenium dioxide/t-butyl hydroperoxide essentially as described in Example 1. After 11.5 hr of oxidation at 4° C. the reaction mixture is poured onto a cooled, brine-saturated mixture of 500 ml of ethyl acetate, 100 mL of 4% aqueous sodium hydroxide and 25 mL of 1% sodium thiosulfate solution. After phase separation the organic layer is washed as described in Example 1 and evaporated yielding a crude product weighing 625.0 mg. Treatment with phenylboronic acid and chromatography in accordance with the procedures of Example 1 gives 58.9 mg of 5,6-trans-1α-hydroxyvitamin $D_2$: UV (EtOH) $\lambda_{max}$ 273 nm; $^1$H NMR (270 MHz) δ0.56 (3H, s, 18-Me), 0.82 and 0.84 (6H, 2 doublets, J 6.5 Hz, 26, 27-Me), 0.92 (3H, d, J 6.1 Hz, 21-Me), 1.02 (3H, d, J 6.5 Hz, 28-Me), 4.23 (1H, m, 3-H), 4.49 (1H, m, 1-H), 4.97 (1H, m (sharp), (19Z)-H), 5.12 (1H, m (sharp), (19E)-H), 5.20 (2H, m, 22,23-H), 5.88 and 6.57 (2H, ABq, J 11.1 Hz, 6- and 7-H). Utilizing procedures essentially similar to that described above, but substituting 24-hydroxyvitamin $D_2$, 25-hydroxyvitamin $D_2$ or 24,25-dihydroxyvitamin $D_2$ for vitamin $D_2$, there is obtained 1α,24-dihydroxy-5,6-trans-vitamin $D_2$, 1α,25-dihydroxy-5,6-trans-vitamin $D_2$ and 1α,24,25-trihydroxy-5,6-trans-vitamin $D_2$, respectively.

EXAMPLE 3

Synthesis of 1α-Hydroxyvitamin D₃ from 5,6-trans-1α-hydroxyvitamin D₃

A portion (58.3 mg) of the product from Example 1 is transferred to a 3-necked, 200 ml, round-bottomed flask equipped with a gas dispersion tube, gas exit bubbler and a thermometer. A charge of 150 mg of anthracene in 150 ml of benzene is added and the resulting solution irradiated at 10° C. (cold room) under a steady stream of nitrogen gas using 3–22 watt, circular fluorescent light bulbs. After 42 h of irradiation, TLC indicates the complete disappearance of a spot co-migrating with 5,6-trans-1α-hydroxyvitamin D₃ and the appearance of a new spot co-migrating with 1α-hydroxyvitamin D₃. After 45 h of irradiation the reaction is worked up by evaporation of the solvent. The residue is taken up in 15 ml of ether and filtered. The precipitate is washed with ether (3 ml, 3×). The combined filtrate and washings are evaporated and the residue applied in benzene to a 1×55 cm silica gel column. The column is eluted with benzene then with ethyl acetate/hexane mixtures, to yield 45 mg of a white powder shown to be identical with 1α-hydroxyvitamin D₃ by comparison of nmr, uv, mass spectra and chromatographic properties with those of an authentic sample of this compound (prepared from 1α-hydroxycholesterol). Utilizing procedures essentially similar to that described above, but substituting other appropriate 5,6-trans-vitamin D compounds for 5,6-trans-1α-hydroxyvitamin D₃, there is obtained 1α-hydroxyvitamin D₂ from 5,6-trans-1α-hydroxyvitamin D₂; 1α,25-dihydroxyvitamin D₃ from 5,6-trans-1α,25-dihydroxyvitamin D₃; 1α,24,25-trihydroxyvitamin D₃ from 5,6-trans-1α,24,25-trihydroxyvitamin D₃; 1α,25,26-trihydroxyvitamin D₃ from 5,6-trans-1α,25,26-trihydroxyvitamin D₃; 1α,24-dihydroxyvitamin D₂ from 5,6-trans-1α,24-dihydroxyvitamin D₂; 1α,25-dihydroxyvitamin D₂ from 5,6-trans-1α,25-dihydroxyvitamin D₂; 1α,24,25-trihydroxyvitamin D₂ from 5,6-trans-1α,24,25-trihydroxyvitamin D₂.

We claim:

1. A process for preparing 1α-hydroxy-5,6-trans-vitamin D compounds which comprises, treating a 5,6-cis-vitamin D compound having the formula

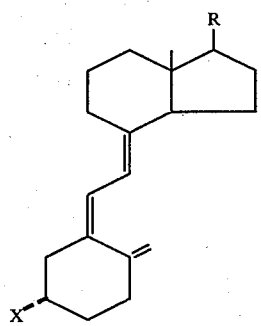

wherein X is selected from the group consisting of hydrogen, hydroxy and protected-hydroxy, and R is any sidechain substituent desired in the 1α-hydroxy-5,6-trans-vitamin D product, with iodine and a mixture of SeO₂ and a hydroperoxide in the presence of organic nitrogenous base, and recovering the desired 1α-hydroxy-5,6-trans-vitamin D product.

2. The process of claim 1 wherein the hydroperoxide is an alkylhydroperoxide.

3. The process of claim 1 wherein the nitrogenous base is selected from the group consisting of pyridine, collidine, picoline, quinoline, and octahydroacridine.

4. The process of claim 3 where the nitrogenous base is pyridine.

5. The process of claim 1 wherein SeO₂ is used in stoichometric amounts relative to vitamin D starting material.

6. The process of claim 1, wherein SeO₂ is used in catalytic amounts relative to vitamin D starting material.

7. The process of claim 1 wherein the 1α-hydroxy-5,6-trans-vitamin D compound is isomerized to the corresponding 1α-hydroxy vitamin D compound by irradiation in the presence of a photosensitizer, and the 1α-hydroxyvitamin D compound is recovered.

8. The process of claim 7 wherein the photosensitizer used is selected from the group consisting of anthracene, phenazine, and acridine.

9. The process of claims 1 or 7 where R is selected from

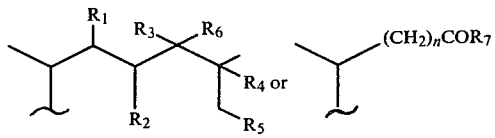

wherein each of R₁ and R₂ is selected from the group consisting of hydrogen, hydroxy, protected-hydroxy, and fluoro, or where R₁ and R₂ when taken together form a double bond or an epoxide grouping, where each of R₃, R₄, and R₅ is selected from the group consisting of hydrogen, hydroxy, protected-hydroxy and fluoro, or where R₃ and R₄, or R₄ and R₅, when taken together form an epoxide grouping or a double bond, where R₆ is selected from the group consisting of hydrogen, alkyl, and fluoro, where R₇ is selected from the group consisting of hydroxy, alkyl and O-alkyl, and n is an integer from about 1 to about 4.

10. A process for separating a vitamin D compound having a 1,3-trans-diol configuration, or a 5,6-trans vitamin D compound having a 1,3-trans-diol configuration, from an epimeric mixture containing said vitamin D compound and the corresponding 1,3-cis-diol epimer, or containing said 5,6-trans vitamin D compound and the corresponding 1,3-cis-diol epimer, which comprises, treating said epimeric mixture with an alkyl or arylboronic acid whereby a cyclic 1,3-boronate ester of the vitamin D compound or the 5,6-trans vitamin D compound having the 1,3-cis-diol configuration is obtained, separating said vitamin D or 5,6-trans-vitamin D boronate ester from the reaction mixture, and recovering the desired vitamin D compound or 5,6-trans-vitamin D compound having a 1,3-trans-diol configuration.

11. A process according to claim 10 wherein the boronic acid used is phenylboronic acid.

12. A process according to claim 10 or 11 wherein the recovered vitamin D compound having a 1,3-trans-diol configuration is a 1α-hydroxyvitamin D compound.

13. A process according to claim 10 or 11 wherein the recovered 5,6-trans-vitamin D compound having a 1,3- trans-diol configuration is a 1α-hydroxy-5,6-trans-vitamin D compound.

14. The process of claim 1 wherein the vitamin D starting material is vitamin $D_3$.

15. The process of claim 1 wherein the Vitamin D starting material is 25-hydroxy-vitamin $D_3$.

16. The process of claim 1 wherein the vitamin D starting material is 24,25-dihydroxyvitamin $D_3$.

17. The process of claim 1 wherein the vitamin D starting material is 25,26-dihydroxyvitamin $D_3$.

18. The process of claim 1 wherein the vitamin D starting material is vitamin $D_2$.

19. The process of claim 1 wherein the vitamin D starting material is 25-hydroxyvitamin $D_2$.

20. The process of claim 1 wherein the vitamin D starting material is 24,25-dihydroxyvitamin $D_2$.

21. The process of claim 1 wherein the vitamin D starting material is 24-hydroxyvitamin $D_2$.

* * * * *